(12) United States Patent
Sherman et al.

(10) Patent No.: US 9,006,606 B2
(45) Date of Patent: Apr. 14, 2015

(54) FLEXIBLE DRILL AND METHOD OF JOINING NITINOL TO DISSIMILAR METALS

(75) Inventors: Gary Scott Sherman, Naples, FL (US); Jerry F. Sterrett, Naples, FL (US)

(73) Assignee: Arthrex, Inc., Naples, FL (US)

( * ) Notice: Subject to any disclaimer, the term of this patent is extended or adjusted under 35 U.S.C. 154(b) by 609 days.

(21) Appl. No.: 13/038,556

(22) Filed: Mar. 2, 2011

(65) Prior Publication Data

US 2011/0218538 A1  Sep. 8, 2011

Related U.S. Application Data

(60) Provisional application No. 61/311,233, filed on Mar. 5, 2010.

(51) Int. Cl.
| | |
|---|---|
| *B23K 26/32* | (2014.01) |
| *A61B 17/16* | (2006.01) |
| *A61B 17/00* | (2006.01) |
| *A61B 17/32* | (2006.01) |

(52) U.S. Cl.
CPC ... *A61B 17/1631* (2013.01); *A61B 2017/00526* (2013.01); *A61B 2017/00867* (2013.01); *A61B 2017/00871* (2013.01); *A61B 2017/320032* (2013.01)

(58) Field of Classification Search
CPC ............... A61B 17/1631; A61B 2017/00526; A61B 2017/00867; A61B 2017/00871; A61B 2017/320032
USPC ............... 219/121.63, 121.64, 121.6, 121.85; 228/153, 154, 165, 172, 174, 262.41, 228/262.3, 262.44; 606/80
See application file for complete search history.

(56) References Cited

U.S. PATENT DOCUMENTS

| | | | |
|---|---|---|---|
| 3,095,951 A * | 7/1963 | Rood et al. | 403/272 |
| 6,645,159 B1 * | 11/2003 | Burkett | 600/585 |
| 2003/0087117 A1 * | 5/2003 | Duley et al. | 219/121.64 |
| 2003/0191487 A1 | 10/2003 | Robinson et al. | |
| 2004/0182835 A1 | 9/2004 | Hall | |
| 2005/0082773 A1 * | 4/2005 | Julien | 280/11.12 |
| 2005/0187537 A1 | 8/2005 | Loeb et al. | |
| 2006/0012095 A1 * | 1/2006 | Bjorkgard et al. | 269/40 |
| 2006/0047223 A1 | 3/2006 | Grandfield et al. | |
| 2006/0184188 A1 * | 8/2006 | Li et al. | 606/180 |
| 2006/0235505 A1 * | 10/2006 | Oepen et al. | 623/1.15 |
| 2007/0199926 A1 * | 8/2007 | Watanabe et al. | 219/121.64 |
| 2007/0233039 A1 * | 10/2007 | Mitelberg | 604/523 |
| 2009/0326538 A1 | 12/2009 | Sennett et al. | |
| 2010/0049240 A1 * | 2/2010 | Papp | 606/200 |
| 2011/0147080 A1 * | 6/2011 | Slininger et al. | 174/84 R |

FOREIGN PATENT DOCUMENTS

| | | |
|---|---|---|
| WO | WO 03/039378 A1 | 5/2003 |
| WO | WO 03/039379 A1 | 5/2003 |

* cited by examiner

*Primary Examiner* — Dana Ross
*Assistant Examiner* — James Sims, III
(74) *Attorney, Agent, or Firm* — Dickstein Shapiro LLP

(57) ABSTRACT

A flexible drill with a shaft having a nitinol portion (or nitinol region) provided between a stainless steel driver end and a stainless steel drill tip. The flexible drill with nitinol shaft is provided with a bearing surface to allow centering within a drill guide, low friction bearing and flexibility to drill around a curve. The bearing surface may be formed of a fluoropolymer such as LDPE (Low Density Polyethylene). The flexible drill shaft may be used through a drill guide, such as a curved drill sleeve.

1 Claim, 4 Drawing Sheets

*Section A-A*

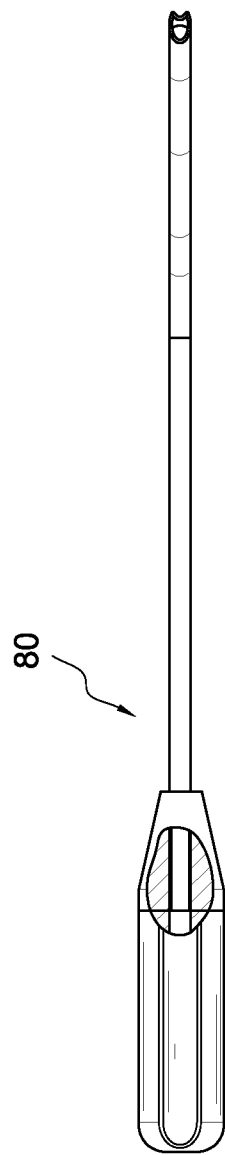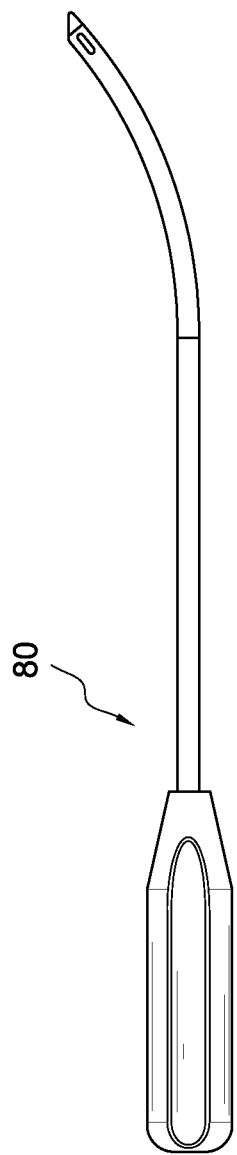

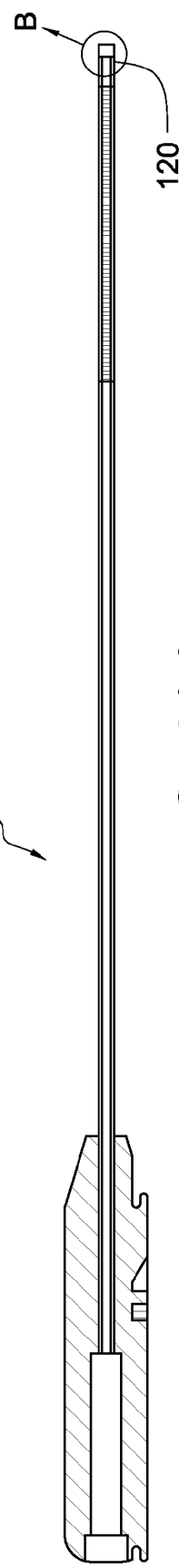
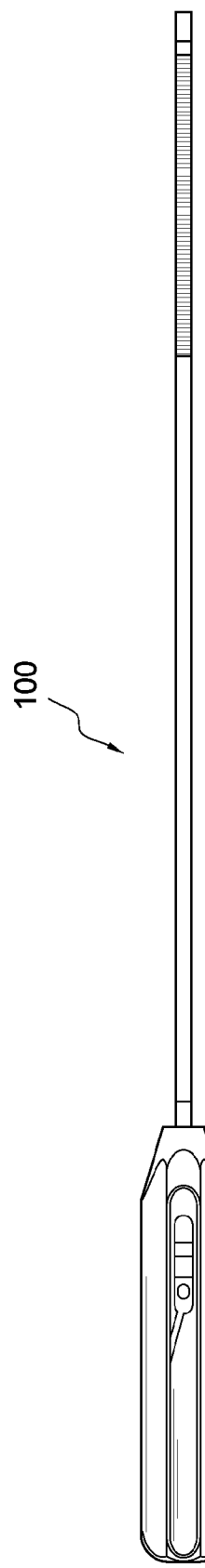
FIG. 6(a)
FIG. 6(b)
FIG. 6(c) Detail B

FLEXIBLE DRILL AND METHOD OF JOINING NITINOL TO DISSIMILAR METALS

CROSS-REFERENCE TO RELATED APPLICATIONS

This application claims the benefit of U.S. Provisional Application No. 61/311,233, filed Mar. 5, 2010, the entire disclosure of which is incorporated by reference herein.

FIELD OF THE INVENTION

The present invention relates to arthroscopic surgical methods and instruments and, more specifically, to a flexible drill instrument using a nitinol shaft and a low friction bearing, and to methods of joining a nitinol shaft portion to a shaft portion formed of a dissimilar metal such as stainless steel.

BACKGROUND OF THE INVENTION

Surgical cutting instruments in which an inner member is rotated within a tubular outer member are known in the art. Typically, the tubular outer member includes a distal end with an opening defining a cutting port or window and the inner member includes a distal end with a cutting tip for engaging bodily tissue via the opening. Proximal ends of the inner and outer members commonly include hubs which attach to a handpiece having a motor for rotating the inner member relative to the outer member. The distal end of the inner member can have various configurations dependent upon the surgical procedure to be performed, with the opening in the distal end of the outer member being suitably configured to cooperate with the particular configuration of the distal end of the inner member to cut, resect or abrade tissue.

Often the tubular inner and outer members are straight. In many surgical procedures, however, it is desirable for the cutting instruments to be bent or curved to access surgical sites which are generally not accessible with straight cutting instruments. For example, in arthroscopic knee, hip or shoulder surgery it is well known to use curved cutting instruments which can be positioned at various desired angles relative to the surface of the bone.

The present invention provides a flexible drill which includes a nitinol portion of the shaft, to increase the flexibility of the shaft while maintaining sufficient column strength for the instrument during a cutting/drilling operation. Also provided is a novel method of joining (welding) a nitinol portion of a shaft to an adjacent portion of a shaft formed of a dissimilar metal, for example, joining (welding) a nitinol portion of a shaft to an adjacent stainless steel portion of the shaft.

SUMMARY OF THE INVENTION

The present invention provides a flexible drill with a shaft having a nitinol portion (or nitinol region) provided between a stainless steel driver end and a stainless steel drill tip. The flexible drill using the nitinol shaft of the present invention may be provided with a bearing surface to allow centering within a drill guide, low friction bearing and flexibility to drill around a curve. The bearing surface may be formed of a polymer, for example, a fluoropolymer of tetrafluoroethylene such as polytetrafluoroethylene (PTFE) or LDPE (Low Density Polyethylene). The novel drill shaft of the present invention may be preferably used through a drill guide such as a curved drill sleeve.

The invention also provides a method of joining (directly welding or fusing) nitinol (nickel-titanium alloy) to a dissimilar metal by inter alia: (i) providing cross-holes in a tubular member formed of a material dissimilar to nitinol; (ii) inserting a nitinol piece to be welded within at least a portion of the tubular member; and (iii) creating "plug" welds using laser in the cross-holes.

These and other features and advantages of the invention will be more apparent from the following detailed description that is provided in connection with the accompanying drawings and illustrated exemplary embodiments of the invention.

BRIEF DESCRIPTION OF THE DRAWINGS

FIG. 5a illustrates a top view of a curved drill guide into which the flexible drill of the present invention is passed;

FIG. 5b illustrates a side view of the curved drill guide of FIG. 5a;

FIG. 6a illustrates a partial cross-sectional view of a driver with a flexible shaft for placing an anchor through the sleeve once the flexible drill has created a hole in bone for receiving the anchor;

FIG. 6b illustrates a top view of the driver of FIG. 6a; and

FIG. 6c illustrates an enlarged view of the most distal end of the driver of FIG. 6a.

DETAILED DESCRIPTION OF THE PREFERRED EMBODIMENTS

Figure 1:
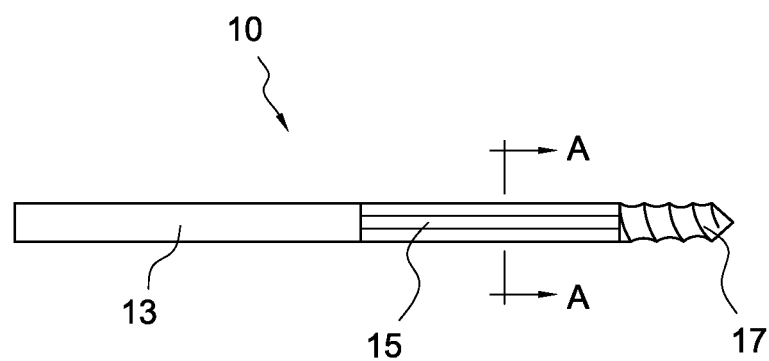
FIG. 1 illustrates a lateral view of a flexible drill shaft of the present invention (with a nitinol shaft provided between a drive end and a drill tip)

The following description is provided to enable any person skilled in the art to make and use the invention and sets forth the best modes contemplated by the inventors of carrying out their invention. Various modifications, however, will remain readily apparent to those skilled in the art.

The present invention provides a flexible drill with a shaft having a nitinol portion (or nitinol region) provided between a stainless steel driver end and a stainless steel drill tip. The flexible drill with nitinol shaft of the present invention may be provided with a bearing surface to allow centering within a drill guide, low friction bearing and flexibility to drill around a curve. The bearing surface may be formed of a polymer, for example, a fluoropolymer of tetrafluoroethylene such as polytetrafluoroethylene (PTFE) or LDPE (Low Density Polyethylene). The novel drill shaft of the present invention may be preferably used through a drill guide such as a curved drill sleeve.

The invention also provides a method of joining (directly welding or fusing) nitinol (nickel-titanium alloy) to a dissimilar metal by inter alia: (i) providing cross-holes in a tubular member formed of a material dissimilar to nitinol; (ii) inserting a nitinol piece to be welded within at least a portion of the tubular member; and (iii) creating "plug" welds using laser in the cross-holes.

The invention also provides a method of joining (directly welding) a first member formed of nitinol to a second member formed of a dissimilar metal such as stainless steel (or a material similar to stainless steel). The method of the present invention comprises inter alia the steps of: (i) providing a first member formed of nitinol adjacent a second member formed of a dissimilar metal; (ii) drilling a plurality of cross-holes through the second member formed of dissimilar metal; (iii) inserting the first member to be welded within the second member; and (iv) creating "plug" welds using laser in the cross-holes, to keep the weld away from the joint regions (high stress regions).

The invention also provides a method of joining (directly welding) materials which have different physical and chemical characteristics, for example, for joining (directly welding) nitinol to a dissimilar metal such as stainless steel or a material similar to stainless steel. The method of the present invention comprises inter alia the steps of: (i) providing a part of a shaft formed of nitinol adjacent another part of the shaft formed of a dissimilar metal; (ii) drilling a plurality of cross-holes through the part of the shaft formed of dissimilar metal; (iii) inserting the part of the shaft formed of nitinol to be welded within the dissimilar metal part; and (iv) creating "plug" welds using laser in the cross-holes, to keep the weld away from the joint regions (high stress regions). In this manner, the heat is kept away from the high stress regions (i.e., the regions which are subjected to most torque during the flexing and/or bending of the shaft).

In an exemplary only embodiment, the method of the present invention comprises inter alia the steps of: (i) providing a rigid part of a shaft formed of stainless steel adjacent a flexible part of the shaft formed of nitinol; (ii) drilling a plurality of cross-holes through the rigid part of the shaft formed of stainless steel; (iii) inserting the flexible part of the shaft formed of nitinol to be welded within the stainless steel part; and (iv) creating "plug" welds using laser in the cross-holes, to keep the weld away from the joint regions (high stress regions). The rigid part of the shaft may be a driver end or a drill tip.

Figure 2:
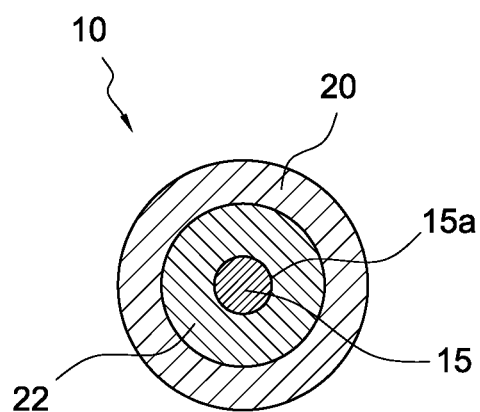
FIG. 2 illustrates an enlarged cross-sectional view of the flexible, nitinol portion of the flexible drill shaft of FIG. 1, taken along line A-A.

Referring now to the drawings, where like elements are designated by like reference numerals, FIGS. 1 and 2 illustrate a flexible drill 10 with a shaft having a flexible nitinol portion 15 (or nitinol region 15 or core region 15) provided between a rigid driver end 13 and a drill tip 17, both the driver end 13 and the drill tip 17 being formed of a dissimilar material, i.e., a material which is substantially different from nitinol, such as for example, stainless steel or other ferrous material.

In an exemplary embodiment only, flexible drill 10 comprises a shaft having a flexible nitinol portion 15 (a nitinol core or wire 15) that consists essentially of nitinol and that is placed between, and in direct contact, with a rigid stainless steel driver end 13 (a cut tubular member 13) and a rigid stainless steel drill tip 17. The flexible nitinol portion 15 may be in the form of a core or wire 15 or, alternatively, in the shape of a cut tubular member 15. The nitinol portion 15 is essentially formed of a shape-memory alloy with superelastic properties, for example, a psuedoelastic alloy material preferably consisting essentially of about 30 to about 52% titanium with the balance nickel and optionally up to 10% of one or more other alloying elements (which are selected from the group consisting of iron, cobalt, vanadium, platinum, palladium and copper).

The nitinol shaft 15 is centered in the drill guide and cannot unwind, yet providing flexibility to drill around a curve. The flexible drill 10 using the flexible nitinol shaft of the present invention is provided with a coating 20, for example, a polymeric coating such as a PTFE or LDPE (Low Density Polyethylene) bearing surface 20 to allow centering within the drill guide (shown in FIGS. 5a and 5b), low friction bearing and flexibility to drill around a curve. The polymeric coating may be applied by co-extrusion, spray coating or other surface deposition techniques known in the art. If LDPE is employed for the bearing surface 20, the LDPE material may be preferably provided on the nitinol region by injection molding to save processing time.

FIG. 2 is a cross-sectional view of the flexible portion or region 15 of the flexible drill 10 of FIG. 1, taken along line A-A of FIG. 1. As shown in FIG. 2, flexible nitinol portion 15 is in the form of a nitinol core 15 (nitinol wire 15) which is surrounded by a flexible filler 22, which in turn is provided between the nitinol surface 15a and the polymeric coating for bearing 20. The flexible filler 22 may be silicone or a $Si_2C$ variant or a similar material. The flexible filler 22 may be provided on substantially the whole length/surface of the nitinol surface 15a of the nitinol wire 15 or, alternatively, may be provided at least on a nitinol surface located at a distal end and a proximal end of the flexible nitinol region 15 (to allow joining of the nitinol to the driver end the drill tip formed of a dissimilar metal such as stainless steel).

The novel drill shaft of the present invention is preferably used through a curved drill sleeve. FIGS. 5a and 5b illustrate a top view and a side view, respectively, of a curved drill guide 80 into which the flexible drill 10 of the present invention is passed. The flexible nitinol shaft 15 is centered in the curved drill guide 80 and cannot unwind, yet provides flexibility to drill around a curve. FIGS. 6a and 6b illustrate a driver 100 which is used to place an anchor in the hole in bone formed by the flexible drill of the present invention. FIG. 6c illustrates an end view of the most proximal end 102 of the driver 100.

By using nitinol in the distal section only of the shaft of the flexible drill 10 and a more economical material metal tube (such as a more cost-effective alloy like stainless steel) in the proximal section, both the performance and the overall design of the shaft are optimized. The desired connection between nitinol and stainless steel is achieved without causing deficiencies in the strength and behavioral properties of the ends of nitinol shaft attached, on each side, to the stainless steel members (i.e., to the rigid driver end 13 and the rigid drill tip 17).

Figure 3:
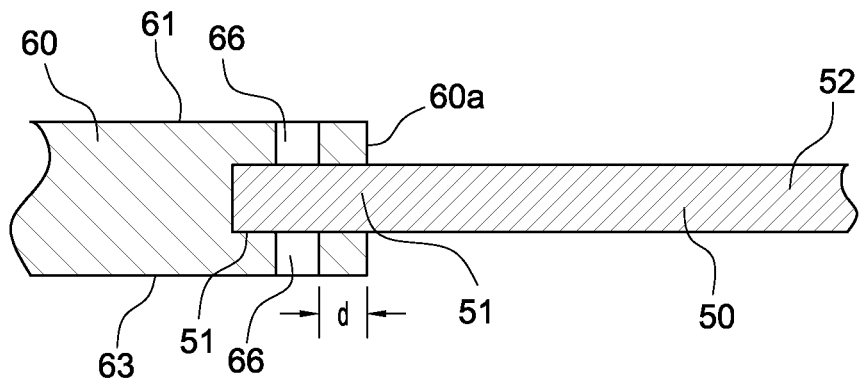
FIG. 3 illustrates a cross-sectional partial view of a shaft undergoing welding of a nitinol portion to a stainless steel portion, and according to a method of joining different materials of the present invention.
Figure 4:
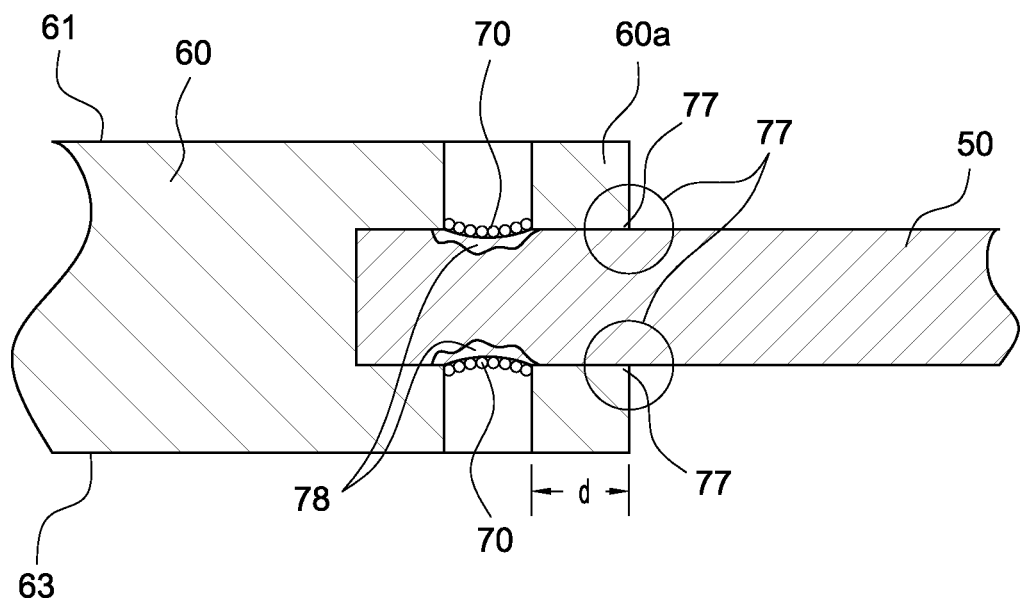
FIG. 4 illustrates an enlarged view of the welding regions of the shaft of FIG. 3, depicting the heat affected zones (by the welding) and the high stress zones (which are not affected by the welding)

Reference is now made to FIGS. 3 and 4 which detail a method of joining different materials of the present invention (for example, nitinol and stainless steel). Although the embodiment below will be explained with reference to joining/welding/fusing of two specific dissimilar materials, i.e., nitinol and stainless steel, the invention is not limited to this particular exemplary embodiment only, and has applicability to the joining/welding/fusing of nitinol (or nickel-titanium alloys) to any other dissimilar metal (i.e., any metal in addition to stainless steel).

FIG. 3 illustrates a partial cross-sectional view of a shaft/tubular member undergoing joining/welding of a nitinol portion 50 (nitinol shaft or core, or first member 50) to a stainless steel portion 60 (stainless steel shaft or second tubular member 60), and according to a method of joining different materials of the present invention. The method comprises inter alia the steps of: (i) providing a first member 50 formed of nitinol adjacent a second tubular member 60 formed of a dissimilar metal; (ii) drilling a plurality of cross-holes 66 through the second tubular member 60 formed of dissimilar metal; (iii) inserting the first member 50 within the second tubular member 60; and (iv) creating "plug" welds 70 using laser in the cross-holes 66, to keep the weld away from the joint regions 77 (high stress regions 77). In an exemplary embodiment only, the nitinol portion 50 corresponds to the flexible nitinol core or wire 15 of FIG. 1, and the stainless steel portion 60 corresponds to the stainless steel driver end 13 or the driver tip 17 of FIG. 1. Second tubular member may be a solid member or, alternatively, a cannulated member.

Cross-holes 66 are provided at a distance "d" (FIGS. 3 and 4) from the most distal end 60*a* of second tubular member 60 to ensure that the heat (and the heat affected zones 78 (FIG. 4)) are kept away from the high stress regions, which are the regions where the joints between nitinol and the dissimilar metal (stainless steel) occur (i.e., the regions between the stainless steel distal portion 60*a* and the nitinol proximal portion 51). Holes 66 are formed by drilling across the diameter of the tubular member 60 (i.e., from a top surface 61 to a bottom surface 63). Once the nitinol member 50 is inserted within the second member 60, cross-holes interface the top surface 50*a* of the nitinol member 50.

Joining/welding of the nitinol to the dissimilar metal may be achieved by fusion welding such as pulse laser welding, cladding or alloying using laser. These laser joining processes essentially include laser heating of areas where the two different metals (the nitinol and the stainless steel) interface, i.e., at the bottoms of holes 66.

FIG. 4 illustrates an enlarged view of the welding region of the shaft of FIG. 3, depicting the heat affected zones 78 (by the welding) and the unaffected high stress zones 77 (which are not affected by the welding and which correspond to the interface between most distal end 60*a* of stainless steel member 60 and proximal end 51 of nitinol wire 50).

The laser welds the bottom of the holes 66 and eliminates the need for additional pieces of intermediary material (such as a nickel piece) provided between the stainless steel shaft and the nitinol shaft, to facilitate welding of these two dissimilar materials. The method of the present invention provides a simpler, faster and more efficient way of welding nitinol to a material different from it (such as stainless steel).

Although the invention above has been described with reference to a specific nitinol wire and a specific tubular stainless steel member, the invention is not limited to these specific and illustrative only embodiments and has applicability to any structure in any form such as, for example, ribbon, sheet, bar, solid wire, stranded wire, braided wire, etc., which allow the formation of cross-holes and the insertion of the nitinol member within the dissimilar metal member.

The invention provides an improved, simpler and faster method of laser joining a first nitinol member to a second member, with no intermediate material necessary (for example, with no intermediate piece or material disposed between the nitinol member and the second tubular member).

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of joining nitinol to a dissimilar metal, comprising the steps of
    providing a tubular nitinol member consisting essentially of a nitinol wire with a nitinol core and covered by a coating for surface bearing in the proximity of a tubular member of a dissimilar metal, a diameter of the tubular nitinol member being smaller than a diameter of the tubular member of the dissimilar metal, wherein the nitinol wire forms a flexible part of a shaft of a surgical drill, and the tubular member is a stainless steel shaft forming a rigid part of the shaft of the surgical drill;
    forming a plurality of cross-holes through the tubular member by drilling across a diameter of the tubular member from a top surface to a bottom surface, the plurality of cross-holes extending in a direction perpendicular to a longitudinal axis of the tubular member;
    inserting the nitinol member within the tubular member so that the cross-holes interface a top surface of the nitinol member; and
    joining the nitinol member directly to the tubular member of the dissimilar metal by conducting fusion welding by creating welding plugs in the cross-holes using laser while keeping the welding away from joint regions therefore allowing heat to be kept away from high stress regions which are subjected to most torque during flexing or bending of the shaft, wherein joining the nitinol member directly to the tubular member of the dissimilar metal is conducted with no intermediate piece or material disposed between the nitinol member and the tubular member.

* * * * *